United States Patent [19]

Scheffler et al.

[11] Patent Number: 4,623,742
[45] Date of Patent: Nov. 18, 1986

[54] OXAZAPHOSPHORIN-4-THIO-ALKANE-SULPHONIC ACIDS, AND NEUTRAL SALTS THEREOF

[75] Inventors: Gerhard Scheffler; Ulf Niemeyer; Norbert Brock, all of Bielefeld; Jörg Pohl, Halle, all of Fed. Rep. of Germany

[73] Assignee: ASTA-Werke Aktiengesellschaft Chemische Fabrik, Belefeld, Fed. Rep. of Germany

[21] Appl. No.: 683,374

[22] Filed: Dec. 19, 1984

Related U.S. Application Data

[63] Continuation-in-part of Ser. No. 356,636, Mar. 10, 1982, abandoned.

[30] Foreign Application Priority Data

Mar. 24, 1981 [DE] Fed. Rep. of Germany ....... 3111428

[51] Int. Cl.$^4$ .............................................. C07F 9/21
[52] U.S. Cl. ...................................................... 558/81
[58] Field of Search ........................................ 260/936;
558/81 (U.S. only)

[56] References Cited

U.S. PATENT DOCUMENTS 4,238,423 12/1986 Sato et al. ............................ 260/936
4,239,709 12/1980 Sato ..................................... 260/936

FOREIGN PATENT DOCUMENTS 3220432 12/1983 Fed. Rep. of Germany ...... 260/936
3220672 12/1983 Fed. Rep. of Germany ...... 260/936
2095256 9/1982 United Kingdom ................ 260/936

OTHER PUBLICATIONS

Brock et al., "Drug Research", vol. 26, (1979), pp. 659–661.
Carter et al, "Chemotherapy of Cancer", 2nd Edition, (1981), pp. 26–43.

Primary Examiner—Anton H. Sutto
Attorney, Agent, or Firm—Pearne, Gordon, Sessions, McCoy, Granger & Tilberry

[57] ABSTRACT

This invention relates to new oxazaphosphorin-4-thio-alkanesulphonic acids and to the neutral salts thereof corresponding to the general formula I

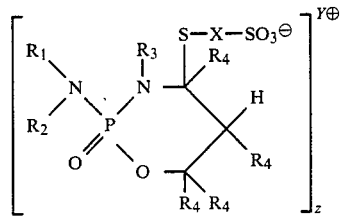

and to methods to use such compounds to control cancer diseases and to produce immunosuppression in humans and animals.

6 Claims, No Drawings

OXAZAPHOSPHORIN-4-THIO-ALKANESULPHONIC ACIDS, AND NEUTRAL SALTS THEREOF

This is a continuation-in-part application of copending application Ser. No. 356,636, filed Mar. 10, 1982, now abandoned.

This invention relates to new oxazaphosphorin-4-thio-alkanesulphonic acids and to neutral salts thereof corresponding to the general formula I:

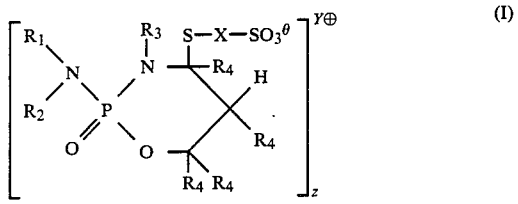

in which $R_1$, $R_2$ and $R_3$, which may be the same or different, represent hydrogen, methyl, ethyl, 2-chloroethyl or 2-methanesulphonyloxyethyl and, at least two of these radicals represent 2-chloroethyl and/or 2-methanesulphonyloxyethyl, $R_4$ represents hydrogen or methyl, X represents a straight- or branched-chain $C_{2-6}$-alkylene group which may have a mercapto group at the carbon atom in the 1, 2, 3, 4 or 5 position in the alkylene chain, and $Y^\oplus$ represents a hydrogen cation, an alkali metal or alkaline earth metal cation, a guanidinium, morpholinium or cyclohexylammonium cation or a cation which is derived from an amine of formula $NR_5R_6R_7$, in which the radicals $R_5$ to $R_7$ are the same or different and represent hydrogen, a $C_1$-$C_2$ alkyl group or an oxyethyl group, or Y represents an ethylenediammonium cation ($H_3N^\oplus$—$CH_2CH_2$—$N^\oplus H_3$) or an piperazonium cation, and z represents 1 when $Y^\oplus$ is a mono-basic cation, or represents 2 when $Y^\oplus$ is a di-basic cation or the cation of a compound having two mono-basic cations. The cis-configuration of the compounds and the neutral salts thereof are distinguished due to their improved stability Due to their easy accessibility and good properties those compounds of formula I are preferred, in which $Y^\oplus$ represents the guanidinium, morpholinium or cyclohexylammonium cation or the cation which is derived from an amine of the formula $NR_5R_6R_7$, wherein the radicals $R_5$ to $R_7$ are the same or different and represent hydrogen, $C_1$-$C_2$ alkyl groups or oxyethyl groups, or in which $Y^\oplus$ represents the ethylenediammonium cation ($H_3N^\oplus$—$CH_2CH_2$—$N^\oplus H_3$) or the piperazonium cation, and z represents 1 when $Y^\oplus$ represents a mono-basic cation, or represents 2 when $Y^\oplus$ represents a di-basic cation or the cation of a compound having two mono-basic cations.

The potassium and alkaline earth metal salts of the acids of formula I also have other favourable properties and are preferred for this reason.

Among the acids of formula I which are neutralized with nitrogen bases, the following are most particularly preferred: the ammonium salts, in which $Y^\oplus$ represents the $NH_4^\oplus$ cation, the cyclohexylammonium salts, in which $Y^\oplus$ represents the $C_6H_{11}NH_3^\oplus$ cation, or the guanidinium salts in which $Y^\oplus$ represents the $N^\oplus H_2=C(NH_2)$ cation.

The cis-sodium-2-[2-(bis-(2-chloroethyl)-amino)-2-oxo-tetrahydro-2H-1,3,2,-oxazaphosphorin-4-yl]-thioethanesulphonate and the corresponding ammonium, cyclohexylammonium and potassium salts are particularly easily accessible and are thus preferred among the salts according to the present invention.

Compounds of formula I in which $R_1$ and $R_2$ represent the 2-chloroethyl group, $R_3$ and $R_4$ represents hydrogen, X represents the ethylene group and z=1 and $Y^\oplus = NH_4^\oplus$,

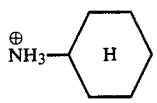

or $N^\oplus H_2=C(NH_2)_2$ or $X=(CH_2)_3$, $z=1$, and $Y=N^\oplus H_2=C(NH_2)_2$ are particularly significant.

The oxazaphosphorin-4-thio-alkanesulphonic acids according to the present invention and neutral salts thereof corresponding to the general formula I can be obtained according to the present invention by reacting a 4-hydroxy- or 4-$C_{1-4}$ alkoxy-oxazaphosphorin corresponding to the following general formula II:

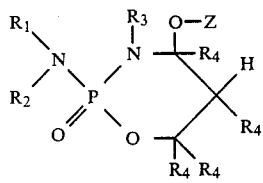

wherein $R_1$, $R_2$, $R_3$ and $R_4$ have the same meanings as in formula I, and Z represents hydrogen or $C_{1-4}$ alkyl, with a compound corresponding to the general formula III:

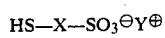

wherein X and $Y^\oplus$ have the same meanings as in formula I, and if $Y^\oplus$ represents hydrogen, the oxazaphosphorin-4-thio-alkanesulphonic acid which is obtained is neutralised with one of these bases corresponding to the other meanings of $Y^\oplus$.

The following solvents are suitable: water, alcohols, in particular alkanols having from 1 to 6 carbon atoms, such as methanol, ethanol, propanol or isobutanol, alkyl ketones having in each case from 1 to 4 carbon atoms, such as in particular acetone, methylethylketone, dimethylformamide (DMF), hexamethylphosphoric acid-triamide, halogenated hydrocarbons having from 1 to 3 carbon atoms, such as chloroform and ethylenedichloride, tetrahydrofuran, diethylether or similar solvents or mixtures of several such solvents. The reaction is carried out at a temperature ranging from −60° to +80° C., preferably from −30° to +60° C. and in particular from −30° to +40° C., i.e., optionally with cooling, at room temperature or with heating. The reaction may be carried out in the presence of an acid catalyst, such as an organic or inorganic acid, in particular such as trichloroacetic acid or a Lewis acid, such as $AlCl_3$, $ZnCl_2$ or $TiCl_4$.

The cation $Y^\oplus$ of a sulphonate according to formula I may be exchanged for another cation, for example, in a correspondingly charged ion exchanger. This exchange is advisable in those cases in which it is difficult to produce a salt having a specific cation $Y^\oplus$ by the process of the present invention. The required salt may thus be obtained in a high yield from another salt which is easy to produce.

The new compounds of formula I are isolated by conventional working-up processes for such products, in particular by crystallisation, precipitation or chromatographic purification, in particular on Sephadex. The structure is verified by the melting point, by thin layer chromatography, by elementary analysis or by IR and NMR spectral analysis.

The compounds which are used as the starting material in the process of the present invention are known, may be used in crystalline form or as crude product and may be synthesized in a known manner as follows:

4-Hydroxy-oxazaphosphorins are obtained by reduction of the 4-hydroperoxy derivatives (for example, A. Takamizawa et al., J. Amer. Chem. Soc. 95, 589 (1973) and German Offenlegungsschrift No. 2,317,178).

4-Alkoxy-oxazaphosphorins are formed with acid catalysis from the hydroxy derivatives in the corresponding alcohol. The thiols are obtained by the reaction of the corresponding sodium bromoalkanesulphonate with thiourea to produce the thiouronium salt which is split with ammonia and converted into the required salt of the mercaptoalkanesulphonate.

If $Y^\oplus$ represents an alkali metal cation, this is in particular the sodium or potassium salt. If $Y^\oplus$ represents an alkaline earth metal cation, this is in particular a neutral calcium or magnesium salt. If $Y^\oplus$ represents a cyclohexyl ammonium cation, then it is the following cation:

$$C_6H_{11}NH_3^\oplus;$$

if $Y^\oplus$ represents the following cation:

$$R_5R_6R_7N^\oplus,$$

then this cation may be derived in particular from the following amines: methylamine, ethylamine, dimethylamine, diethylamine, trimethylamine, triethylamine, methylethylamine, dimethylethylamine, diethylmethylamine, 2-hydroxy-ethylamine, bis-(2-hydroxy-ethyl)-amine, tris-(2-hydroxy-ethyl)-amine, (2-hydroxy-ethyl)-methylamine, (2-hydroxy-ethyl)-dimethylamine, bis-(2 hydroxy-ethyl)-methylamine, (2-hydroxy-ethyl)-ethylamine, (2-hydroxy-ethyl)-diethylamine, bis-(2-hydroxy-ethyl)-ethylamine, and (2-hydroxy-ethyl)-methylethylamine.

The term "the oxazaphosphorin derivatives corresponding to formula I according to the present invention" is to be understood to include all four possible stereoisomers, i.e., the two racemic cis-isomers and the two racemic trans-isomers, and the four separate optically active cis-isomers and trans-isomers and mixtures thereof. The cis/trans-mixtures may be separated in known manner, preferably by fractional crystallisation. Optically active compounds may be obtained by conventional methods of resolution, for example by fractional crystallisation of the diastereomeric salts of the racemic sulphonic acid of formula I with optically active bases or optionally by using optically active starting materials according to formula II in the synthesis.

Counting of the position of the mercapto group in the alkylene group X starts at the carbon atom carrying the sulfonic acid group.

Cis/trans-mixtures are usually produced during the synthesis. Thus, in the case of compounds which are easily crystallisable, the cis- or the trans-form, in particular the cis-form can be obtained therefrom by crystallisation. However, if the reaction is carried out in anhydrous solvents or in solvents containing a small amount of water, a single form, in particular the cis-form is obtained exclusively or predominantly. Thus, the pure cis-form of a non-crystallising compound or of a poorly crystallising compound according to formula I may be produced, for example, by a process in which a solution of the compound according to formula II in acetone is added to an aqueous solution of the compound according to formula III at a temperature of from $-30°$ to $+20°$ C. and the product is dissolved and reprecipitated several times after the reaction has been completed.

The starting compounds according to formula II may be used as racemic cis- and trans-isomers (production given above), as the optically active cis- and trans-form and as mixtures thereof. Optically active compounds according to formula II are obtained, for example, from the salts of the optically active sulphonic acids (production given above), by a process in which they are hydrolysed into the corresponding optically active 4-hydroxy-oxazaphosphorins of formula II (in water, for example, from $0°$ to $50°$ C., in particular from $5°$ to $30°$ C.) and the thiol of formula III which is produced is oxidized into a disulphide (for example, using iodine or hydrogen peroxide in water). Another process is based, for example, on a separate optically active cyclophosphamide derivative according to Example 16 or 33 of U.S. patent application No. 299,006 filed 9-30-81, and this compound is hydrolysed into the optically active 4-hydroxy-cyclophosphamide. In another process, optically active cyclophosphamide for example (German Offenlegungsschrift No. 2,944,106) is converted into optically active 4-hydtoxy-cyclophosphamide by the process which is described by Peter et. al, in Cancer Treatment Reports 60, 429 (1976).

Examples of optically active bases for resolution are as follows: 1-phenylethylamine, brucine, chinidine, strychnine and cinchonine and other bases and methods which are described in "Optical Resolution Procedures for Chemical Compounds", Volume 2, Paul Newman, 1981, Verlag Optical Resolution Information Center in Riverdale, U.S.A. These optically active bases may also be used during the synthesis according to the reaction of a compound of formula II with a compound of formula III, instead of the meanings of Y which have already been given. In this case, this optically active base is then exchanged in conventional manner for hydrogen or for another base Y corresponding to the definition of Y which has already been given.

Another process for the production of the oxazaphosphorin-4-thio-alkanesulphonic acids and the neutral salts thereof of formula I is characterised in that a 4-hydroxy-or 4-$C_{1-4}$ alkoxy-oxazaphosphorin corresponding to the general formula II:

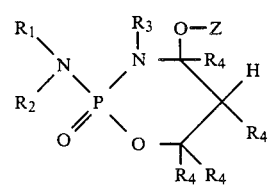

II wherein $R_1$, $R_2$, $R_3$ and $R_4$ are as defined in formula I and Z represents hydrogen or $C_{1-4}$ alkyl, is reacted with a compound corresponding to the general formula III $$HS-X-SO_3^{\ominus}Y^{\oplus}$$

wherein X is as defined in formula I and $Y^{\oplus}$ is derived from an optically active base which does not correspond to the definition of Y given in formula I and after the reaction this other optically active base is exchanged for hydrogen or for a base corresponding to the definition of Y given in formula I.

The cis-compounds and the neutral salts thereof according to the present invention are distinguished by their improved stability as demonstrated hereinafter. In contrast therewith, the trans-configuration compounds and salts thereof, alone or in mixture with the cis-configuration compounds and salts, are not stable and tend to decompose so as to preclude pharmaceutical usage.

The stability of the compounds and neutral salts in the cis-configuration according to the present invention is demonstrated by comparison with the sodium salt indicated to be contained in the urine of test animals treated with cyclophosphamide in Brock et al., *Drug Research*, Vol. 29, (1979), pages 659–661. Such sodium salt is a mixture of both configurations in a weight ratio of about 60% cis-configuration and about 40% trans-configuration. Both configurations have the following formula and the cis-configuration has been determined by X-ray structural analysis.

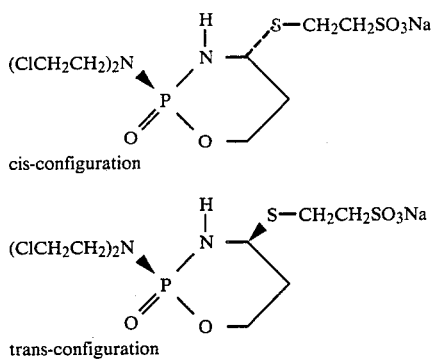

cis-configuration trans-configuration

The foregoing sodium salt mixture is synthesized as follows for comparison with various salts of oxazaphosphorin-(4)-mercaptoalkane herein.

2.8 g. (10 mmole) of 4-hydroxy-cyclophosphamide and 1.15 g. (7 mmole) of sodium 2-mercaptoethane-sulfonate are dissolved in 3 ml of water together with a trace of trichloroacetic acid (pH about 2.5) and are left to stand for 15 hours at 5° C. 10 ml of acetone are then added and the mixture is concentrated under vacuum at 20° C. The residue is taken up in 20 ml of acetone and dry ether is added thereto resulting in a precipitation of a colorless oil. This oil is again dissolved in acetone and the product again precipitated by the addition of dry ether. This procedure is repeated until a solid precipitate is obtained. This solid precipitate is filtered off with suction and washed with ether and dried over $P_2O_5$ under vacuum. Yield: 1.3 g. The thin-layer chromotogram shows two spots; Rf-value: 0.48 (cis-configuration, about 60%) and 0.46 (trans-configuration, about 40%); eluant: ethyl acetate; isopropanol: 1N acetic acid 50:35:25.

The stability of the foregoing sodium salt mixture of the cis-/trans-configuration is compared below with the pure cis-2-[2-(bis-(2-chloroethyl-amino)-2-oxo-tetrahydro-2H-1,3,2-oxazaphosphorin-4-yl-thio]-ethane sulfonic acid sodium salt of Example 32 of this application and the other indicated cis-configuration salts. The test compounds according to the present invention shown in the table below were stored for 5 months at +20° C. Thereafter, the test compounds were examined chromotographically for products of decomposition.

| Salt (Cation) | Temperature of Storage, °C. | Stability After 5 months of storage |
|---|---|---|
| Sodium salt, pure cis-configuration | +20 | (1) |
| Cyclohexylammonium salt, pure cis-configuration | +20 | (1) |
| Ammonium salt, pure cis-configuration | +20 | (1) |
| Guanidinium salt, pure cis-configuration | +20 | (1) |

Foot note:
(1) = no significant decomposition, white powders.

The above table shows, that all of the salts according to the subject application at 20° C. are stable upon storage for at least 5 months.

Contrary thereto, the cis-/trans-mixture produced as noted above changes into a yellowish product considerably contaminated by products of decomposition after 3 days of storage at 20° C. Therefor, the cis-/trans-mixture shows no usefulness as an active agent in a drug since drugs are quite often stored in the pharmacy for the above test period of 5 and more months.

The foregoing comparison demonstrates that the cis-/trans-configuration of the salt compound, as disclosed in Brock et al., supra, does not comprise a compound useful as an active agent in pharmaceutical applications, as contrasted to the cis-configuration. The improvement in stability demonstrated by the compounds of the present invention is a prerequisite for use in drugs and such was not suggested by the prior art.

The compounds of the present invention may be used to control cancer and for immunosuppression. They have a strong anti-tumour activity and are distinguished by a high activity in parenteral and oral application and by low generally toxic. phenomena. In vivo, they have a high carcinotoxic selectivity and in vitro, they have a high cytotoxic specifity.

In order to establish the carcinotoxic effect, the substances were tested experimentally on animals, on a series of tumours of different chemoresistance. To evaluate the results, the mean doses which were effective in curative terms (ED 50 [mg/kg]) were determined using the probit analysis from the relation between logarithms of the doses and the frequencies of cured and surviving experimental animals. The standard compound cyclophosphamide which is closely related in its chemical constitution with the products according to the present invention was used as a comparative material.

In the case of lymphatic leukemia L5222 of rats (strain: BD IX), the mean curative dose in a single intraveneous application on the fifth day after inoculating the leukemia was 1.5 mg/kg for the products of the present invention as well as for cyclophosphamide.

In the case of chemosensitive Yoshida-Aszites-carcinosarcoma (line AH 13) of rats (strain: Sprague-Dawley), the $ED_{50}$ value was 1 mg/kg for the products of the present invention as well as for the comparative substance cyclophosphamide.

The toxicity was tested in an analogous manner, in which test, the average fatal dose ($LD_{50}$ [mg/kg]) was determined from the relation between the logarithms of the doses and the death frequency.

This $LD_{50}$ is about 300 mg/kg in a single intravenous application for the products according to the present invention. The mean fatal dose of cyclophosphamide which was determined in comparison is 244 mg/kg in a single intravenous application. Accordingly, the products of the present invention have an acute toxicity which is lower by about 20% or have a correspondingly higher therapeutic scope with the same curative efficiency.

For examining the cytotoxic specifity in vitro, in each case about $3 \times 10^7$ cells of the chemoresistant Yoshida-Aszites-carcinosarcoma (line AH 13, origin ASTA) obtained under sterile conditions were incubated for two hours at 37° C. with increasing concentrations of the products according to the present invention, and after being repeatedly washed out, were implanted in the abdominal cavity of untreated host animals. The average cytotoxic doses ($CE_{50}$ [μg/ml]) were determined using the probit analysis from the relation between the logarithms of the concentrations and the frequencies of developing tumours Under these experimental conditions, the $CE_{50}$ of the products according to the present invention is from 3 to 5 μg/ml.

Since cyclophosphamide does not have a cytotoxic activity in that it is an initially inactive form of transport compound, the active primary metabolite 4-hydroxycyclophosphamide was used in these experiments as the comparative substance, which is formed in the body by enzymatic activation, and is mainly formed in the liver. The average cytotoxic concentration is also 5 μg/ml for this comparative substance.

The compounds according to the present invention are suitable for the production of pharmaceutical compositions and preparations. The pharmaceutical compositions or medicaments contain as the active substance one or more of the compounds according to the present invention, optionally in admixture with other pharmacologically or pharmaceutically active substances. The medicaments are produced in a known manner, and the known and conventional pharmaceutical auxiliaries and other conventional carriers and diluents may be used.

The substances which are specified or recommended in the following references as auxiliaries for pharmacy, cosmetics and related fields are included, for example, as the carriers and auxiliaries: Ullmanns Encyklopädie der technischen Chemie, Volume 4 (1953) pages 1 to 39; Journal of Pharmaceutical Sciences, Volume 52 (1963), page 918 and ff. H.v.Czetsch-Lindenwald, Hilfsstoffe für Pharmazie und angrenzende Gebiete; Pharm. Ind., No. 2, 1961, page 72 and ff.; Dr. H. P. Fiedler, Lexikon der Hilfsstoffe für Pharmazie, Kosmetik und angrenzende Gebiete, Cantor KG. Aulendorf in Württemberg 1971.

The following are included as examples of such substances: gelatin, natural sugars, such as cane sugar or lactose, lecithin, pectin, starch (for example, corn starch), alginic acid, tylose, talcum, lycopodium, silica (for example, colloidal silica), cellulose, cellulose derivatives (for example, cellulose ethers in which the cellulose hydroxy groups are partly etherified with lower saturated aliphatic alcohols and/or lower saturated aliphatic oxyalcohols, for example methyloxypropylcellulose), stearates, magnesium and calcium salts of fatty acids having from 12 to 22 carbon atoms, in particular the saturated fatty acids (for example, stearates), emulsifying agents, oils and fats, in particular vegetable oils and fats (for example, arachis oil, castor oil, olive oil, sesame oil, cottonseed oil, corn oil, wheatgerm oil, sunflower seed oil, cod-liver oil, mono-, di- and triglycerides of saturated fatty acids $C_{12}H_{24}O_2$ to $C_{18}H_{36}O_2$ and the mixtures thereof), pharmaceutically acceptable mono- or polyhydric alcohols and polyglycols, such as polyethylene glycols and derivatives thereof, esters of aliphatic saturated or unsaturated fatty acids (from 2 to 22 carbon atoms, in particular from 10 to 18 carbon atoms) with monohydric aliphatic alcohols (from 1 to 20 carbon atoms) or polyhydric alcohols, such as glycols, glycerol, diethylene glycol, pentaerythritol, sorbitol, mannitol etc., which may optionally also be etherified, benzyl benzoate, dioxolanes, glycerol formals, tetrahydrofurfuryl alcohol, polyglycol ethers with $C_1$-$C_{12}$ alcohols, dimethyl acetamide, lactamides, lactates, ethylcarbonates, silicones (in particular medium-viscosity dimethyl polysiloxanes), magnesium carbonate and the like.

Water or physiologically acceptable organic solvents are included, for example, to prepare solutions, as for example, ethanol, 1,2-propylene glycol, polyglycols and the derivatives thereof, dimethylsulphoxide, fatty alcohols, triglycerides, partial esters of glycerol, paraffins and the like.

Known and conventional solubilizers or emulsifying agents may be used for the production of the preparations. The following are included, for example, as solubilizers and emulsifying agents: polyvinylpyrrolidone, sorbitan fatty acid esters, such as sorbitan trioleate, lecithin, acacia, tragacanth, polyoxyethylated sorbitan monooleate, polyoxyethylated fats, polyoxyethylated oleotriglycerides, linolised oleotriglycerides, polyethyleneoxide condensation products of fatty alcohols, alkylphenols, or fatty acids or also 1-methyl-3-(2-hydroxyethyl)-imidazolidone-(2). The term "polyoxyethylated" in this context means that the relevant substances contain polyoxyethylene chains, the degree of polymerisation of which is generally from 2 to 40 and in particular from 10 to 20. Such polyoxyethylated substances may be obtained, for example, by reacting compounds containing hydroxyl groups (for example, mono- or diglycerides or unsaturated compounds, for example those which contain oleic acid radicals) with ethyleneoxide (for example, 40 mols of ethyleneoxide per mol of glyceride). Examples of oleotriglycerides include olive oil, arachis oil, castor oil, sesame oil, cottonseed oil, and corn oil (also see Dr. H. P. Fiedler "Lexikon der Hilfsstoffe für Pharmazie, Kosmetik und angrenzende Gebiete 1971, page 191 to 195).

Moreover, it is possible to add preservatives, stabilisers, buffers, for example calcium hydrogen-phosphate colloidal aluminium hydroxide, flavour correctants, antioxidants and complex formers (for example, ethylenediaminotetra-acetic acid) and the like. To stabilize the active substance molecule, the pH range may have to be adjusted to about 3 to 7 using physiologically acceptable acids or buffers. In general, a pH value as near as possible to neutral to mildly acid (up to pH 5) is preferred The following are used, for example, as antioxidants: sodium metabisulphite, ascorbic acid, gallic acid, gallic acid alkylesters, butylhydroxyanisole, nordihydroguaiaretic acid, tocopherols and tocopherols+synergists (substances which bind heavy metals by complex formation, for example lecithin, ascorbic acid and phosphoric acid). The addition of synergists considerably increases the antioxidant effect of the tocopherols. The following are included, for example, as preservatives: sorbic acid, p-hydroxybenzoic acid esters (for example, lower alkylesters), benzoic acid, sodium benzoate, trichloroisobutyl alcohol, phenol, cresol, benzethonium chloride and formalin derivatives.

The compounds according to the present invention are pharmaceutically and galenically handled according to the conventional standard methods. For example, active substance(s) and aids or carrier materials are thoroughly mixed by stirring or homogenising (for example, using conventional mixing devices), this operation generally being carried out at temperatures of from 20° to 80° C., preferably from 20° to 50° C. and in particular at room temperature. Reference is made, moreover, to the following standard publication: Sucker, Fuchs, Speiser, Pharmazeutische Technologie, Thieme-verlag Stuttgart, 1978.

The active substances or the medicaments may be applied onto the skin or mucous membranes or inside the body, for example oral, enteral, pulmonary, rectal, nasal, vaginal, lingually, intraveneous, intra-arterial, intracardial, intramuscular, intraperitoneal, intracutaneous, subcutaneous, intrapleural, intrathecal or intracavital administration.

In particular the addition of other active medicaments is also possible or favourable especially uroprotectors such as the soidum salt of 2-mercaptoethanesulphonic acid or the disodium salt of the corresponding disulphide of the formula $HO_3S-CH_2CH_2SSCH_2CH_2-SO_3H$ but also other systemically or locally detoxificating active substances.

The compounds according to the present invention exhibit a good cytostatic and curative efficiency in an intraveneous, intraperitoneal or oral application in different experimental tumours in rats and mice.

Examples of such indications include the following: leukemias, lymphogranulomatosis, lymphosarcoma, reticulosarcoma, plasmocytoma, M. Waldenström; tumour growths which have spread, in particular ovarial, mammary and bronchialcarcinoma, neuroblastoma, testicular tumours, renal carcinomas, pancreatic carcinomas, seminoma, Ewing's sarcoma, post-operative additional treatment, in particular for chemosensitive tumours which have presumably already exceeded the local limits and do not have a good prognosis in spite of a radical operation.

Furthermore, the compounds according to the present invention are particularly suitable for the following uses, in contrast to the known agents "cyclophosphamide" and "ifosfamide":

(1) for local perfusion into the extremities and the large body cavities, (2) for an in vitro-treatment of bone marrow in the extra-corporeal treatment of the bone marrow of leukemia sufferers;

(3) for pre-therapeutic sensitivity tests of tumours in vitro.

For example, the compounds of the present invention are administered to the rat intraveneously, intraperitoneally or orally in different doses five days after the intraperitoneal implantation of $10^5$ cells of the leukemia L5222, and a curative effect is obtained depending on the dose. The recidive- and metastasis-free survival of the tumours carrying animals after 90 days is defined as cure. The dose with which 50% of the tumour-carrying animals may be cured is calculated as the average curative dose $ED_{50}$ from the frequency of cures obtained with the different doses by probit analysis according to R. Fischer.

For example, the compounds of the present invention are also administered intraveneously, intraperitoneally or orally in different doses one day after the intraperitoneal implantation of $10^6$ cells of the Yoshida-Aszites-sarcoma $AH_{13}$ and a curative effect is obtained depending on the dose. In this case as well, the curative effect is defined as the recidive- and metastasis-free survival of the tumour-carrying animals over 90 days.

Accordingly, the dose with which 50% of the tumour-carrying animals may be cured is calculated as the average curative dose ($ED_{50}$) by probit analysis according to R. Fischer.

For example, the compounds according to the present invention are also administered intraveneously, intraperitoneally or orally in different doses, once or repeatedly (four times) on successive days after the intraperitoneal implantation of $10^6$ cells of mouse leukemia L1210 and a cytostatic effect is obtained.

The cytostatic efficiency is to be considered as an extension of the median survial time of the animals which have tumours and is expressed as the dose-dependent percent extension of the survival time compared to an untreated control group. The average curative dose in the case of the rat tumours ranges from 0.1 to 10 mg/kg, independently of the form of administration. An extension of the median survival time of 100% may be achieved with the same doses in the case of mouse leukemia L1210 (see N. Brock: Pharmakologische Grundalgen der Krebs-Chemotherapie In: A. GEORGII (Hrsg), Verhandlungen der Deutschen Krebsgesellschaft volume 1, pp. 15–42, Gustav Fischer Verlag, Stuttgart (1978)). This curative and cytostatic effect is comparable with the effect of the known drugs cyclophosphamide (Endoxan ®) and Ifosfamide (Holoxan ®). The lowest dose which is already effective curatively or cytostatically in the above-mentioned animal experiments is the following, for example:

0.01 mg/kg orally
0.01 mg/kg intraperitoneally
0.01 mg/kg intraveneously.

The following general dosage ranges can be used, for example, for a curative and cytostatic effect (animal experiments as above):

oral administration from 0.01–100 mg/kg in particular from 0.1–10.0 mg/kg intraperitoneal administration from 0.01–100 mg/kg, in particular from 0.1 to 10.0 mg/kg, intraveneous administration from 0.01–100 mg/kg, in particular from 0.1 to 10.0 mg/kg.

Indications for the compounds of the present invention may include: malignant diseases which affect animals.

The pharmaceutical preparations generally contain from 1 mg to 1 g, preferably from 10 to 300 mg of the active component(s) of the present invention.

The preparations may be administered, for example, in the form of tablets, capsules, pills, coated tablets, suppositories, ointments, jellies, creams or in liquid form. Examples of liquid formulations are oily, alcoholic or aqueous solutions, suspensions and emulsions. Tablets which contain from 10 to 200 mg, or solutions which contain from 0.1 to 5% of active substance are a preferred form of use.

The individual dose of the active components according to the present invention may lie, for example, within the following limits:

(a) from 1 to 100 mg/kg, preferably from 10 to 60 mg/kg for oral formulations, (b) from 1 to 100 mg/kg, preferably from 10 to 60 mg/kg for parenteral formulations (for example, intraveneous or intramuscular formulations), (c) from 1 to 100 mg/kg, preferably from 10 to 60 mg/kg for formulations for rectal or vaginal application;

(d) from 1 to 100 mg/kg, preferably from 10 to 60 mg/kg for formulations for local application onto the skin and mucous membranes (for example, in the form of solutions, lotions, emulsions and ointments etc.).

(In each case, the doses are based on the free base).

For example, a dose of form 1 to 10 tablets containing from 10 to 300 mg of active substance may be prescribed 1 to 3 times per day, or, for example, in an intraveneous injection, one or more 1 to 10 ml ampoules containing from 10 to 250 mg of substance may be prescribed 1 or 2 times per day. In oral administration, the minimum daily dose is, for example, 200, whilst the maximum daily dose should not exceed 5000. A continuous infusion corresponding to the dose over a period of 12 or more hours may also be prescribed in individual cases.

For treating dogs and cats, the individual oral dose is generally from about 10 to 60 mg/kg body weight and the parenteral dose is from about 10 to 60 mg/kg body weight.

For treating horses and cattle, the individual oral dose is generally from about 10 to 60 mg/kg and the individual parenteral dose is from about 10 to 60 mg/kg body weight.

The doses specified on this and on the previous pages also relate to the use of the compounds according to the present invention for immunosuppression.

The acute toxicity of the compounds according to the present invention in mice (expressed by the $LD_{50}$ mg/kg Method according to Miller and Tainter: Proc. Soc. Exper. Biol. a. Med. 57 (1944) 261) in oral application is, for example, from 100 to 1000 mg/kg, or above 1000 mg/kg.

The drugs may be used alone or in admixture with other pharmacologically active substances, in animal medicine and in agricultural medicine.

The following Examples further explain the present invention, without restricting it by so doing.

EXAMPLE 1

2-[2-(bis-(2-chloroethyl)-amino)-2-oxo-tetrahydro-2H-1,3,2-oxazaphosphorin-4-yl-thio]-ethanesulphonic acid cyclohexylammonium salt 5.6 g (20 mmol) of 4-hydroxycyclophosphamide (i.e., 2-(bis (2-chloroethyl)-amino)-4-hydroxy-tetrahydro-2H-1,3,2-oxazaphosphorin-2-oxide) and 4.8 g (20 mmol) of cyclohexylammonium-2-mercaptoethanesulphonate were dissolved in 100 ml of distilled water, mixed with some trichloroacetic acid and left to stand in a refrigerator for 3 days at 0° C. The solvent was then removed under high vacuum, the residue was taken up in acetone, re-concentrated, crystallised from acetone and recrystallised from isopropanol.

Yield: 7.2 g (72% of the theoretical yield), M.p. cis-form.: 149°–151° C.

EXAMPLE 2

2-[2-(bis-(2-chloroethyl)-amino)-2-oxo-tetrahydro-2H-1,3,2-oxazaphosphorin-4-yl-thio]-ethanesulphonic acid cyclohexylammonium salt 2.9 g (10 mmol) of 2-(bis-(2-chloroethyl)-amino)-4-methoxy-tetrahydro-2H-1,3,2-oxazaphosphorin-2-oxide and 2.4 g (10 mmol) of cyclohexylammonium-2-mercaptoethanesulphonate were dissolved with some trichloroacetic acid in 10 ml of dimethylformamide and were stored at −25° C. for 20 hours. After leaving the mixture to stand for another three hours at 0° C., it was mixed with ether until clouding commenced, triturated, the crystallised material was filtered with suction after standing for 20 hours at 0° C., and was washed and dried.

Yield: 4.7 g( 94% of the theoretical yield), m.p. cis-form: 145° C. (decomposition)

Recrystallisation from alcohol/ether, m.p.cis-form: 149°–151° C.

EXAMPLE 3

2-[2-(bis-(2-chloroethyl)-amino)-2-oxo-tetrahydro-2H-1,3,2-oxazaphosphorin-4-yl-thio]-ethanesulphonic acid cyclohexylammonium salt 1.4 g (5 mmol) of 4-hydroxycyclophosphamide and 1.2 g (5 mmol) of cyclohexylammonium-2-mercaptoethanesulphonate were dissolved together with a trace of trichloroacetic acid in 25 ml of methanol and were left to stand overnight in a refrigerator at −25° C. The reaction solution was then concentrated to about 5 ml, ether was added until clouding commenced and the mixture was triturated. The crystallised material was filtered with suction after standing for 20 hours at 0° C., and was washed and dried.

Yield: 2.1 g (84% of the theoretical yield), m.p.cis-form: 143°–145° C.

EXAMPLE 4

2-[2-(bis-(2-chloroethyl)-amino)-2-oxo-tetrahydro-2H-1,3,2-oxazaphosphorin-4-yl-thio]-ethanesulphonic acid sodium salt 2.5 g (5 mmol) of cyclohexylammonium-2-2-(bis-(2-chloroethyl)-amino)-2-oxo-tetrahydro-2H-1,3,2-oxazaphosphorin-4-yl]-thio-ethanesulphonate were dissolved in 25 ml of oxygen-free water and were passed through a cation exchanger column produced by Merck which was charged with sodium ions. The eluate was collected over nitrogen, freeze-dried and the solid residue was dried under vacuum over phosphorus pentoxide.

Yield: 1.9 g (91% of the theoretical yield), m.p.: 78°–83° C. (decomposition),

Rf-value: 0.61 (eluant: ethylacetate/iso-propanol/1N acetic acid (5:3:2)).

EXAMPLE 5

2-[2-(bis-(2-chloroethyl)-amino)-2-oxo-tetrahydro-2H-1,3,2-oxazaphosphorin-4-yl-thio]-ethanesulphonic acid ammonium salt 2.8 g (10 mmol) of 4-hydroxycyclophosphamide and 1.6 g (10 mmol) of ammonium-2-mercaptoethanesulphonate were dissolved together with a catalytic quantity of trichloroacetic acid in 50 ml of water and were left to stand in a refrigerator for 3 days at 0° C. The water was then distilled off under high vacuum, the residue was taken up twice in acetone and concentrated under vacuum. Recrystallisation from acetone/ether.

Yield: 3.9 g (93% of the theoretical yield),
m.p.cis-form: 131°–133° C.

EXAMPLE 6

2-[2-(bis-(2-chloroethyl)-amino)-2-oxo-tetrahydro-2H-1,3,2-oxazaphosphorin-4-yl-thio]-ethanesulphonic acid ammonium salt 2.8 g (10 mmol) of 4-hydroxycyclophosphamide and 1.6 g (10 mmol) of ammonium-2-mercaptoethanesulphonate were dissolved with a catalytic quantity of trichloroacetic acid in 10 ml of dimethylformamide and were stored in a refrigerator at −25° C. for 20 hours. After a further 5 hours at 0° C., the mixture was mixed with ether until clouding commenced and was triturated. The crystallised material was filtered with suction after 1 day at 0° C., washed dried and recrystallised from n-propanol.

Yield: 3.2 g (77% of the theoretical yield) of the cis-form, m.p.: 132° C.

EXAMPLE 7

3-[2-(bis-(2-chloroethyl)-amino)-2-oxo-tetrahydro-2H-1,3,2-oxazaphosphorin-4-yl-thio]-propanesulphonic acid sodium salt 5.4 g (20 mmol) of 4-hydroxycyclophosphamide and 5.2 g (20 mmol) of cyclohexylammonium-3-mercapto-propanesulphonate were dissolved in 100 ml of water, mixed with some trichloroacetic acid and left to stand for 1 day at 0° C. The reaction mixture was then concentrated under vacuum, the concentrated residue was passed through a cation exchanger column charged with sodium ions, the eluate was concentrated under vacuum, the residue was dissolved in dry ethanol, was filtered and precipitated with ether.

Yield: 5.5 g (63% of the theoretical yield),
m.p.: 75°–79° C., Rf-value: 0.64 (eluant: ethylacetate/iso-propanol) 1N acetic acid (5:3:2)).

EXAMPLE 8

2-[2-(bis-(2-chloroethyl)-amino)-2-oxo-tetrahydro-2H-1,3,2-oxazaphosphorin-4-yl-thio]-ethanesulphonic acid sodium salt 1.6 g (5 mmol) of 2-(bis-(2-chloroethyl)-amino)-4-ethoxy-tetrahydro-2H-1,3,2-oxazaphosphorin-2-oxide and 0.8 g (5 mmol) of sodium-2-mercaptoethanesulphonate in 10 ml of dimethylformamide were mixed with a trace of trichloroacetic acid and were stored overnight at −25° C. 20 ml of ether were then added to the reaction solution. The residue was filtered with suction after standing for 20 hours at 0° C., and was washed and dried.

Yield: 1.5 g (71% of the theoretical yield),
m.p. 145° to 150° C. (decomposition),
Rf-value: 0.56.

EXAMPLE 9

2-[2-(bis-(2 chloroethyl)-amino)-2-oxo-tetrahydro-2H-1,3,2-oxazaphosphorin-4-yl-thio]-ethanesulphonic acid 0.8 g (3.0 mmol) of 4-hydroxycyclophosphamide in 3 ml of water were mixed with 420 mg (3.0 mmol) of 2-mercaptoethanesulphonic acid, with ice water cooling. After 1 hour, the mixture was concentrated under high vacuum and was crystallised.

Yield: 1.1 g (92% of the theoretical yield),
m.p.: 75°–78° C.

EXAMPLE 10

2-[2-(bis-(2-chloroethyl)-amino)-2-oxo-tetrahydro-2H-1,3,2-oxazaphosphorin-4-yl-thio]-ethanesulphonic acid 2.0 g (4 mmol) of cyclohexylammonium-2-[2-(bis-(2-chloroethyl)-amino)-2-oxo-tetrahydro-2H-1,3,2-oxazaphosphorin-4-yl]-thioethanesulphonate were dissolved in a little water and were passed through a cation ion exchanger charged with hydrogen ions, with cooling to 4° C. The eluate was then freeze-dried and recrystallised from dimethyl formamide/chloroform.

Yield: 1.2 g (75% of the theoretical yield),
m.p : 75°–78° C., Rf-value: 0.58 (eluant: ethyl acetate/isopropanol/1N acetic acid (5:3:2)).

EXAMPLE 11

2-[2-(bis-(2-chloroethyl)-amino)-2-oxo-tetrahydro-2H-1,3,2-oxazaphosphorin-4-yl-thio]-ethanesulphonic acid ammonium salt 720 mg (1.8 mmol) of 2-[2-(bis-(2-chloroethyl)-amino)-2-oxo-tetrahydro-2H-1,3,2-oxazaphosphorin-4-yl]-thioethane-sulphonic acid were dissolved in a little water, neutralised with ammonia and mixed with 4 ml of acetone. The reaction solution was left to stand overnight at −25° C. The crystallised material was filtered with suction and was recrystallised from methanol/acetone.

Yield: 530 mg (71% of the theoretical yield).
m.p.cis-form: 133°–134° C.

EXAMPLE 12

2-[2-(bis-(2-chloroethyl)-amino)-2-oxo-tetrahydro-2H-1,3,2-oxazaphosphorin-4-yl-thio]-ethanesulphonic acid lithium salt 540 mg (2 mmol) of 4-hydroxycyclophosphamide and 300 mg (2 mmol) of lithium-2-mercaptoethanesulphonate were dissolved together with a trace of trichloroacetic acid in 7 ml of water and were left to stand for 20 hours at 0° C. The reaction mixture was concentrated under vacuum, the residue was taken up in acetone and was filtered. The solution was then concentrated, the residue was dissolved in ethanol, was concentrated, taken up again in ethanol, precipitated with ether and the precipitation was filtered with suction, and was washed and dried.

Yield: 500 mg (61% of the theoretical yield), Rf-value: 0.56 (eluant: ethyl acetate/iso-propanol/1N acetic acid (5:3:2).

EXAMPLE 13

Neutral

2-[2-(bis-2-chloroethyl)-amino)-2-oxo-tetrahydro-2H-1,3,2-oxazaphosphorin-4-yl-thio]-ethanesulphonic acid magnesium salt 1.4 g (5 mmol) of 4-hydroxycyclophosphamide and 750 mg (2.5 mmol) of magnesium-di-2-mercaptoethanesulphonate were dissolved together with some trichloroacetic acid in 15 ml of water and were concentrated under vacuum after 3 days at 0° C. The residue was dissolved in ethanol, was concentrated, taken up again in ethanol, precipitated with ether, filtered with suction, and washed and dried.

Yield: 1.3 g (63% of the theoretical yield),
m.p.: 110°–115° C. (decomposition)

Rf-value: 0.56.

EXAMPLE 14

Neutral
2-[2-(bis-(2-chloroethyl)-amino)-2-oxo-tetrahydro-2H-1,3,2-oxazaphosphorin-4-yl-thio]-ethanesulphonic acid calcium salt 1.4 g (5 mmol) of 4-hydroxycyclophosphamide and 800 mg (2.5 mmol) of calcium-di-2-mercaptoethanesulphonate were dissolved together with some trichloroacetic acid in 15 ml of water, were concentrated under vacuum after 3 days at 0° C., mixed twice with ethanol, concentrated, dissolved in ethanol and precipitated with ether, filtered with suction, and washed and dried.
Yield: 1.3 g (62% of the theoretical yield),
m.p.: 110°-115° C. (decomposition),
Rf-value: 0.56.

EXAMPLE 15

2-[2-(bis-(2-chloroethyl)-amino)-6-methyl-2-oxo-tetrahydro-2H-1,3,2-oxazaphosphorin-4-yl-thio]-ethanesulphonic acid cyclohexylammonium salt 1.45 g (5 mmol) of 2-(bis-(2-chloroethyl)-amino)-4-hydroxy-6-methyl-tetrahydro-2H-1,3,2-oxazaphosphorin-2-oxide and 1.2 g (5 mmol) of cyclohexylammonium-2-mercaptoethanesulphonate were dissolved in 5 ml of water and in 5 ml of acetone, acidified with trichloroacetic acid and left to stand for 20 hours at 0° C. The mixture was then filtered, the filtrate was carefully concentrated under vacuum, the residue was taken up twice in acetone and was concentrated. The residue was then dissolved in acetone, precipitated with ether, and washed with ether and dried.
Yield: 1.4 g (56% of the theoretical yield),
m.p.: 120°-125° C. (decomposition).
Rf-value: 0.61.

EXAMPLE 16

3-[2-(bis-(2-chloroethyl)-amino)-2-oxo-tetrahydro-2H-1,3,2-oxazaphosphorin-4-yl-thio]-2-methyl-propanesulphonic acid sodium salt 277 mg (1 mmol) of 4-hydroxycyclophosphamide and 192 mg (1 mmol) of sodium-2-mercapto-2-methyl-propanesulphonate were dissolved in 4 ml of water, mixed with a trace of trichloroacetic acid and left to stand for 20 hours at 0° C. After being concentrated under vacuum, the residue was dissolved twice in dry ethanol and was reconcentrated and precipitated in alcohol/ether.
Yield: 420 mg (86% of the theoretical yield), Rf-value 0.61.

EXAMPLE 17

6-[2-(bis-(2-chloroethyl)-amino)-2-oxo-tetrahydro-2H-1,3,2-oxazaphosphorin-4-yl-thio]-hexanesulphonic acid sodium salt 277 mg (1 mmol) of 4-hydroxycyclophosphamide and 220 mg (1 mmol) of sodium-6-mercaptohexanesulphonate were dissolved together with a trace of trichloroacetic acid in 4 ml of water and were left to stand for 20 hours at 0° C. The reaction mixture was then carefully concentrated under vacuum, the residue was dissolved twice in dry ethanol and was re-concentrated. The residue was taken up in alcohol and precipitated with ether.
Yield: 350 mg (70% of the theoretical yield), Rf-value:0.58.

EXAMPLE 18

2-[3-(2-chloroethyl)-2-(2-chloroethylamino)-2-oxo-tetrahydro-2H-1,3,2-oxazaphosphorin-4-yl-thio]-ethanesulphonic acid cyclohexylammonium salt 277 mg (1 mmol) of 3-(2-chloroethyl)-2-(2-chloroethylamino)-hydroxy-tetrahydro-2H-1,3,2-oxazaphosphorin-2oxide and 240 mg (1 mmol) of cyclohexylammonium-2-mercaptoethanesulphonate were dissolved in 4 ml of water, mixed with a trace of trichloroacetic acid and stored for 20 hours at 0° C. The reaction mixture which was concentrated under vacuum was dissolved twice in ethanol and re-concentrated. It was then taken up in ethanol and precipitated with ether.
Yield: 340 mg (68% of the theoretical yield),
m.p.: 115°-120° C. (decomposition),
Rf-value: 0.56.

EXAMPLE 19

2-[3-(2-chloroethyl)-2-(bis-(2-chloroethyl)-amino)-2-oxotetrahydro-2H-1,3,2-oxazaphosphorin-4-yl-thio]-ethanesulphonic acid cyclohexylammonium salt 340 mg (1 mmol) of 3-(2-chloroethyl)-2-(bis-(2-chloroethyl)-amino)-4-hydroxy-tetrahydro-2H-1,3,2-oxazaphosphorin-2-oxide and 240 mg (1 mmol) cyclohexylammonium-2-mercaptoethanesulphonate in 2 ml of dimethylformamide were mixed with a trace of trichloroacetic acid and were stored for 2 days at −25° C. The reaction mixture was then precipitated with 20 times the quantity of ether. The residue was washed and dried.
Yield: 400 mg (71% of the theoretical yield),
m.p.: 102°-107° C. (decomposition),
Rf-value: 0.63.
The following compounds were also produced in a manner corresponding to the above Examples:

Examples 20-30
oxazaphosphorin-4-thio-alkanesulphonates corresponding to the following general formula:

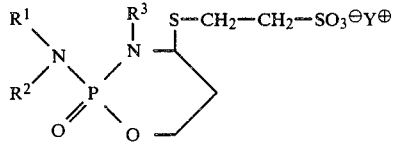

| Example No. | $R^1$ | $R^2$ | $R^3$ | $Y^\oplus$ | Melting point or Rf value[1] |
|---|---|---|---|---|---|
| 20 | Cl—CH$_2$—CH$_2$ | CH$_3$ | | Cl—CH$_2$—CH$_2$ $\overset{\oplus}{N}H_4$ | 121-125° C. (decomp) |

Examples 20–30
oxazaphosphorin-4-thio-alkanesulphonates corresponding to the following general formula:

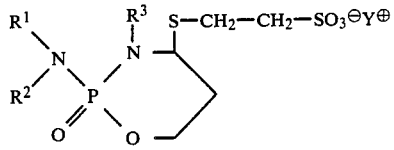

| Example No. | R¹ | R² | R³ | Y⊕ | Melting point or Rf value[1] |
|---|---|---|---|---|---|
| 21 | Cl—CH₂—CH₂ | CH₂—CH₃ | Cl—CH₂—CH₂ | $\overset{\oplus}{N}H_4$ | 95–97° C. (decomp) |
| 22 | CH₃—SO₃—CH₂—CH₂ | CH₃ | Cl—CH₂—CH₂ | cyclohexyl-$\overset{\oplus}{N}H_3$ | 0,64 |
| 23 | Cl—CH₂—CH₂ | Cl—CH₂—CH₂ | H | K⊕ | 120–123° C. (decomp) |
| 24 | Cl—CH₂—CH₂ | Cl—CH₂—CH₂ | H | morpholinium $\overset{\oplus}{N}H_2$ | 70–75° C. (decomp) |
| 25 | Cl—CH₂—CH₂ | Cl—CH₂—CH₂ | H | $(CH_3{-}CH_2)_2\overset{\oplus}{N}H_2$ | 0,61 |
| 26 | Cl—CH₂—CH₂ | Cl—CH₂—CH₂ | H | $HO{-}CH_2{-}CH_2{-}\overset{\oplus}{N}H_3$ | 0,59 |
| 27 | Cl—CH₂—CH₂ | Cl—CH₂—CH₂ | H | $(HO{-}CH_2{-}CH_2)_2\overset{\oplus}{N}H_2$ | 0,59 |
| 28 | Cl—CH₂—CH₂ | Cl—CH₂—CH₂ | H | $NH_2{-}C{=}\overset{\oplus}{N}H_2$ / NH₂ | 132–134° C. |
| 29 | Cl—CH₂—CH₂ | Cl—CH₂—CH₂ | H | $(\overset{\oplus}{H_3N}{-}CH_2{-}CH_2{-}\overset{\oplus}{N}H_3)_{\frac{1}{2}}$ | 0,62 |
| 30 | Cl—CCH₂—CH₂ | Cl—CH₂—CH₂ | H | piperazinium $(H_2\overset{\oplus}{N}\cdots\overset{\oplus}{N}H_2)_{\frac{1}{2}}$ | 0,61 |

[1]Eluant: ethyl acetate/iso-propanol/1N acetic acid (5:3:2)
staining: *inter alia* with iodine.

EXAMPLE 31

3-[2-(bis-(2-chloroethyl)-amino-2-oxo-tetrahydro-2H-1,3,2-oxazaphosphorin-4-yl-thio]-2-mercaptopropanesulphonic acid cyclohexylamine salt 1.39 g (5 mmol) of 4-hydroxycyclophosphamide and 1.44 g (5 mmol) of 2,3-dimercaptopropanesulphonic acid-cyclohexylamine salt were dissolved in 10 ml of ethanol, acidified with trichloroacetic acid and left to stand for 2 days at 0° C. The mixture was then precipitated with ether, decanted after 20 hours and the remaining oil was dried under high vacuum. The oil solidified.
Yield: 1.8 g (77% of the theoretical yield),
m.p.: from 70° C. (decomposition).

EXAMPLE 32

2-[2-(bis-(2-chloroethyl)-amino)-2-oxo-tetrahydro-2H-1,3,2-oxazaphosphorin-4-yl-thio]ethanesulphonic acid cis-sodium salt 2.8 g (10 mmol) of 4-hydroxycyclophosphamide in 10 ml of acetone were mixed with 1.3 g (8 mmol) of sodium-2-mercaptoethane sulphonate in 2 ml of water and were stored for 3 hours at 0° C. The reaction mixture was then concentrated under vacuum at 25° C., the residue was taken up in dry acetone and was mixed with dry ether with cooling until clouding commenced. A deposit formed while the solution was concentrated under vacuum.
Yield: 1.5 g (44% of the theoretical yield) of the cis-isomer,
m.p.: 83°–85° C.
A product which is difficultly soluble in acetone was obtained by recrystallisation in acctone.

EXAMPLE 33

3-[2-(bis-(2-chloroethyl)-amino-2-oxo-tetrahydro-2H-1,3,2-oxazaphosphorin-4-yl-thio]-propanesulphonic acid guanidinium salt 14 g (50 mmol) of 4-hydroxycyclophosphamide and 11 g (50 mmol) of 3-mercaptopropanesulphonic acid guanidine salt were dissolved in 100 ml of ethanol, acidified with trichloroacetic acid and stored at 0° C. After 20 hours, 50 ml of ether were added. The crystallised material was filtered with suction after a further 20 hours, and was washed and dried.
Yield: 18.5 g (78% of the theoretical yield),
m.p.: 128°–132° C. (decomposition).

EXAMPLE 34

Preparations were prepared containing as active substance 50 or 200 mg of the material of Example 23 according to the following summary:

| Compound of Example 23 | 50 mg | 200 mg |
|---|---|---|
| Mannitol | 230 mg | 380 mg |
| Water for injection purposes | up to 2 ml | up to 4 ml |

The compound of Example 23 and mannitol are each dissolved in sufficient water to produce a solution of 2 ml or 4 ml in volume, with gassing with nitrogen and with protection from light. Production and further processing is carried out such that the temperature of the solution does not exceed 5° C. The solutions are subjected in known manner to sterile filtration, 2 ml or 4 ml are metered into brown 10 ml injection flasks under aseptic conditions, provided with freeze-drying stoppers and lyophilized in a freeze-drying installation. The installation is then gassed with dry nitrogen and the ampoule flasks are sealed in the installation.

The residual water content of the substances in the flasks must not exceed 0.5%.

To produce the injection solution which may be administered, the contents of the flasks are dissolved with 50 mg of active substance in 5 ml of water, and with 200 mg of active substance in 10 ml of water for injection purposes.

EXAMPLE 35

Preparations were prepared containing as the active substance 50 or 200 mg of the material of Example 33 according to the following summary:

| Compound of Example 33 | 50 mg | 200 mg |
|---|---|---|
| Mannitol | 245 mg | 430 mg |
| Water for injection purposes | up to 2 ml | up to 4 ml |

The compound of Example 33 and mannitol are each dissolved in sufficient water to produce a solution of 2 or 4 ml in volume, with gassing with nitrogen and with protection from light. Production and further processing is carried out such that the temperature of the solution does not exceed 5° C. The solutions are subjected in a known manner to sterile filtration, 2 ml or 4 ml are metered into brown 10 ml injection flasks under aseptic conditions, provided with freeze-drying stoppers and are lyophilized in a freeze-drying installation. The installation is then gassed with dry nitrogen and the ampoule flasks are sealed in the installation.

The residual water content of the substances in the flasks must not exceed 0.5%.

To produce the injection solution which may be administered, the contents of the flasks are dissolved with 50 mg of active substance in 5 ml of water, and with 200 mg of active substance in 10 ml of water for injection purposes.

What we claim is:

1. The neutral salts in the cis-configuration of oxazaphosphorin-4-thio-alkanesulphonic acids corresponding to formula I

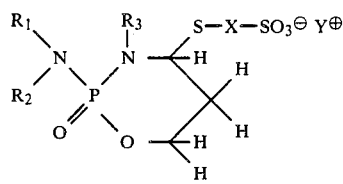

in which
$R_1$ is 2-chloroethyl,
$R_2$ is hydrogen or 2-chloroethyl,
$R_3$ is hydrogen or 2-chloroethyl,
X is $-CH_2-CH_2-$, $-(CH_2)_3-$ or

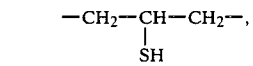

and
$Y^\oplus$ is the cyclohexylammonium, the ammonium, the guanidinium or the sodium cation.

2. The neutral salts according to claim 1 wherein X is $-CH_2-CH_2-$.

3. 2-[2-(Bis-(2-chloroethyl)-amino)-2-oxo-tetrahydro-2H-1,3,2-oxazaphosphorin-4-yl]-thioethane-sulphonic acid cis-sodium salt.

4. 2-[2-(Bis-(2-chloroethyl)-amino)-2-oxo-tetrahydro-2H-1,3,2-oxazaphosphorin-4-yl]-thioethanesulphonic acid cis-ammonium salt.

5. 2-[2-(Bis-(2-chloroethyl)-amino)-2-oxo-tetrahydro-2H-1,3,2-oxazaphosphorin-4-yl]-thio-ethanesulphonic acid cis-cyclohexylammonium salt.

6. 2-[2-(Bis-(2-chloroethyl)-amino)-2-oxo-tetrahydro-2H-1,3,2-oxazaphosphorin-4-yl]-thioethanesulphonic acid cis-potassium salt.

* * * * *